US00PP30861P3

(12) United States Plant Patent
Cerny et al.

(10) Patent No.: US PP30,861 P3
(45) Date of Patent: Sep. 3, 2019

(54) APPLE TREE NAMED 'UEB 42721'

(50) Latin Name: ***Malus domestica* (Borkh.)**
Varietal Denomination: UEB 42721

(71) Applicant: Institute of Experimental Botany AS CR, v.v.i. (UEB), Prague (CZ)

(72) Inventors: Radek Cerny, Ricany u Prahy (CZ); Jan Zima, Turnov (CZ); Otto Louda, Pencin u Liberce (CZ); Jaroslav Tupy, Prague (CZ)

(73) Assignee: Institute of Experimental Botany AS CR, v.v.i. (UEB), Prague (CZ)

( * ) Notice: Subject to any disclaimer, the term of this patent is extended or adjusted under 35 U.S.C. 154(b) by 0 days.

(21) Appl. No.: 15/932,511

(22) Filed: Mar. 8, 2018

(65) Prior Publication Data

US 2018/0263156 P1 Sep. 13, 2018

Related U.S. Application Data

(60) Provisional application No. 62/600,978, filed on Mar. 8, 2017.

(51) Int. Cl.
*A01H 5/00* (2018.01)
*A01H 6/74* (2018.01)

(52) U.S. Cl.
USPC ..... Plt./156
CPC ..... *A01H 6/7418* (2018.05)

(58) Field of Classification Search
USPC ..... Plt./156, 175
See application file for complete search history.

*Primary Examiner* — Susan McCormick Ewoldt
(74) *Attorney, Agent, or Firm* — The Webb Law Firm

(57) ABSTRACT

A new and distinct *Malus domestica* (Borkh.) ornamental variety that exhibits a columnar tree growth type, very narrow growth habit that is generally free of side branches, $V_f$-resistance against scab, attractive red-purple flowers, greyed-purple young leaves, and small, red to red-purple colored, broadly globose shaped fruits that persist on the tree after the fall of leaves until the end of Winter. The new variety is suitable for home apple growing as solitary trees and can be useful for pollinating purposes.

8 Drawing Sheets

Botanical classification: *Malus domestica* (Borkh.).
Varietal denomination: 'UEB 42721'.

BACKGROUND OF THE INVENTION

The present invention comprises a new and distinct cultivar of apple tree botanically classified as *Malus domestica* (Borkh.) and known by the varietal name 'UEB 42721'.

The new variety is the result of a cross in a planned breeding program between 'Evereste' (female parent, unpatented) and 'Maypole' (male parent, U.S. Plant Pat. No. 6,184). The cross resulting in 'UEB 42721' occurred in the Spring of 2003 at 310 meters above sea level with a mean annual temperature of 7.7° C. and a mean annual precipitation of 680 mm. The purpose of the breeding program was to develop an ornamental apple variety having a unique appearance with a columnar tree growth type that exhibits $V_f$-resistance against scab. The new variety was discovered in 2009 with the first flowering and fruiting of the original seedling in the Czech Republic. Subsequently, the new variety was asexually reproduced in Pencin u Liberce in the Czech Republic by budding/grafting on apple rootstocks in the Spring of 2014.

The new variety is similar to its female parent, 'Evereste', in exhibiting small fruits with no russeting present and $V_f$-resistance against scab. However, 'UEB 42721' exhibits a columnar tree growth type, red-purple flower petals, and red to red-purple fruit skin color, while 'Evereste' exhibits a ramified tree growth type, white flower petals, and yellow fruit skin color with an orange to red blush present. The new variety is similar to its male parent, 'Maypole', in exhibiting a columnar tree growth type, red-purple flower petals, and long fruit stalk. However, 'UEB 42721' differs from 'Maypole' in exhibiting fruits that persist longer, are smaller in size, and are broadly globose in shape versus round-conical in shape.

Further, when compared to apple tree named 'UEB 42723' (U.S. Plant patent application Ser. No. 15/932,513, concurrently applied-for herewith), both varieties exhibit a columnar tree growth type and $V_f$-resistance against scab. However, 'UEB 42721' exhibits an erect growth habit and a broadly globose fruit shape, while 'UEB 42723' exhibits a compact growth habit and an ovoid fruit shape.

The following characteristics also distinguish the new variety from other varieties known to the breeders:

- Late ripening, ornamental, diploid variety;
- Columnar tree growth type;
- Very narrow, erect, and compact growth habit with short internodes;
- Weak to medium tree vigor;
- Red-purple color of unopened and open flowers;
- Medium time to beginning of flowering;
- Greyed-purple color of young leaves and green tinted color of mature leaves;
- Fruit is small in size and broadly globose in shape;
- Very long time of fruit persistence; and
- Resistance against scab on $V_f$-gene basis.

The new variety has been trial and field tested and has been found to retain its distinctive characteristics and remain true to type through successive asexual propagations.

DESCRIPTION OF THE DRAWINGS

The accompanying photographic drawings illustrate the new cultivar taken at varying ages of maturity as recited further below, with the color being as nearly true as possible with color illustrations of this type. It should be noted that colors may vary with growing conditions and time of year.

DESCRIPTION OF THE PLANT

Figure 1:
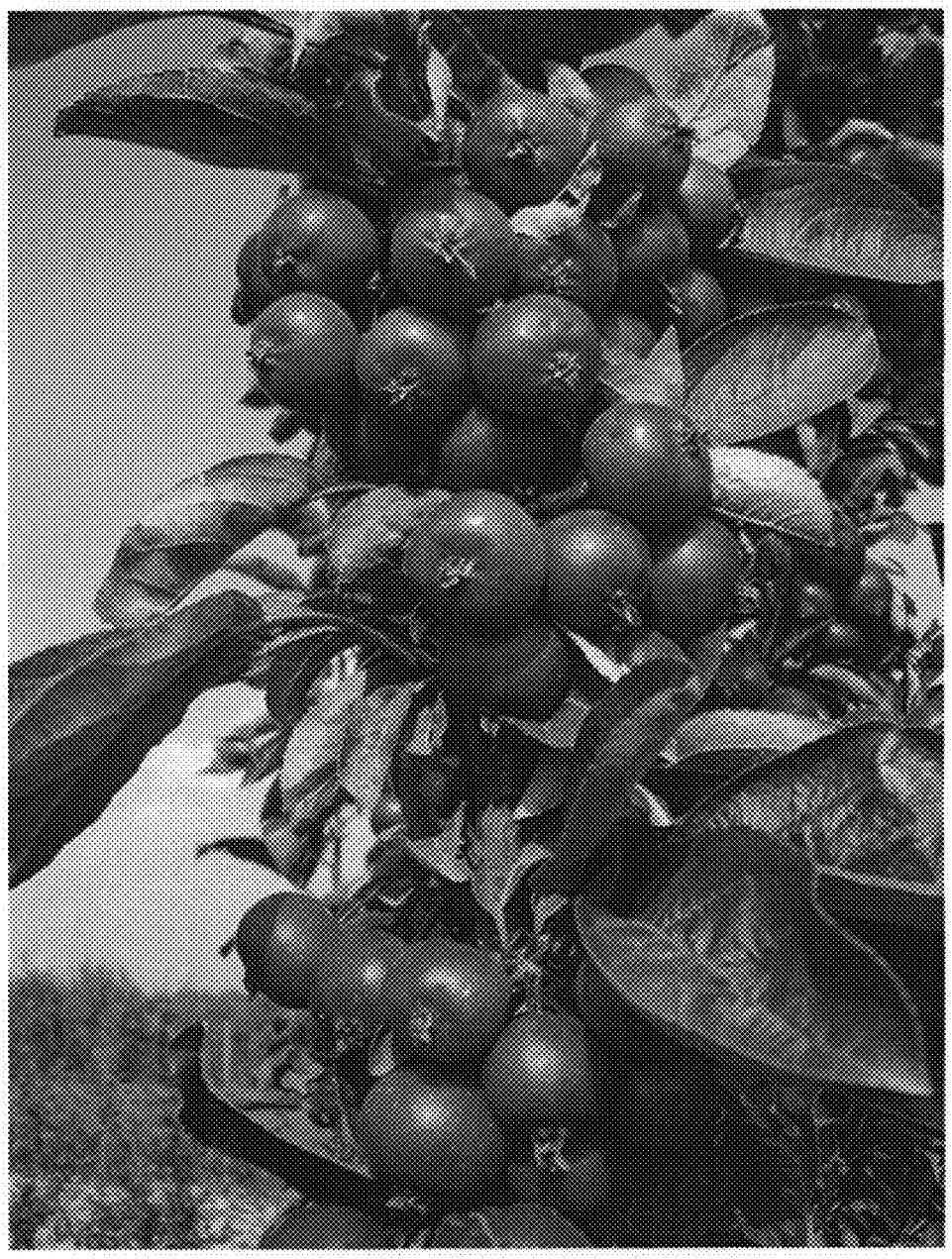
FIG. 1 illustrates a section of the vertical trunk of the new variety at 2 years from grafting, showing details of its ornamental fruits.
Figure 2:
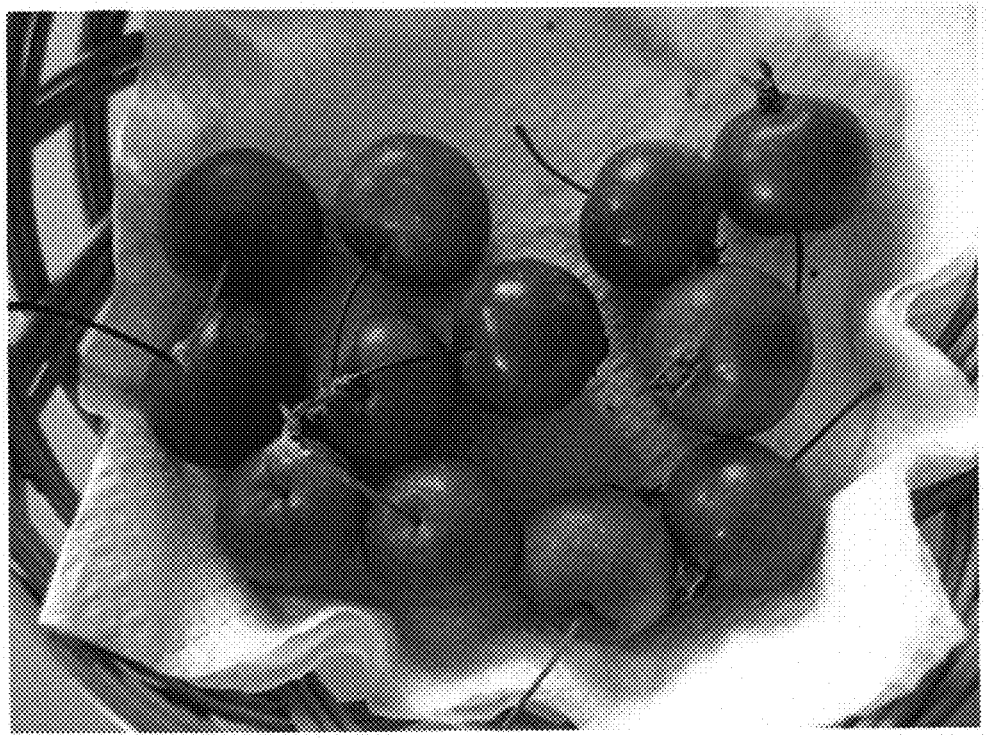
FIG. 2 illustrates details of fruits of the new variety from a 5-year old tree.
Figure 3:
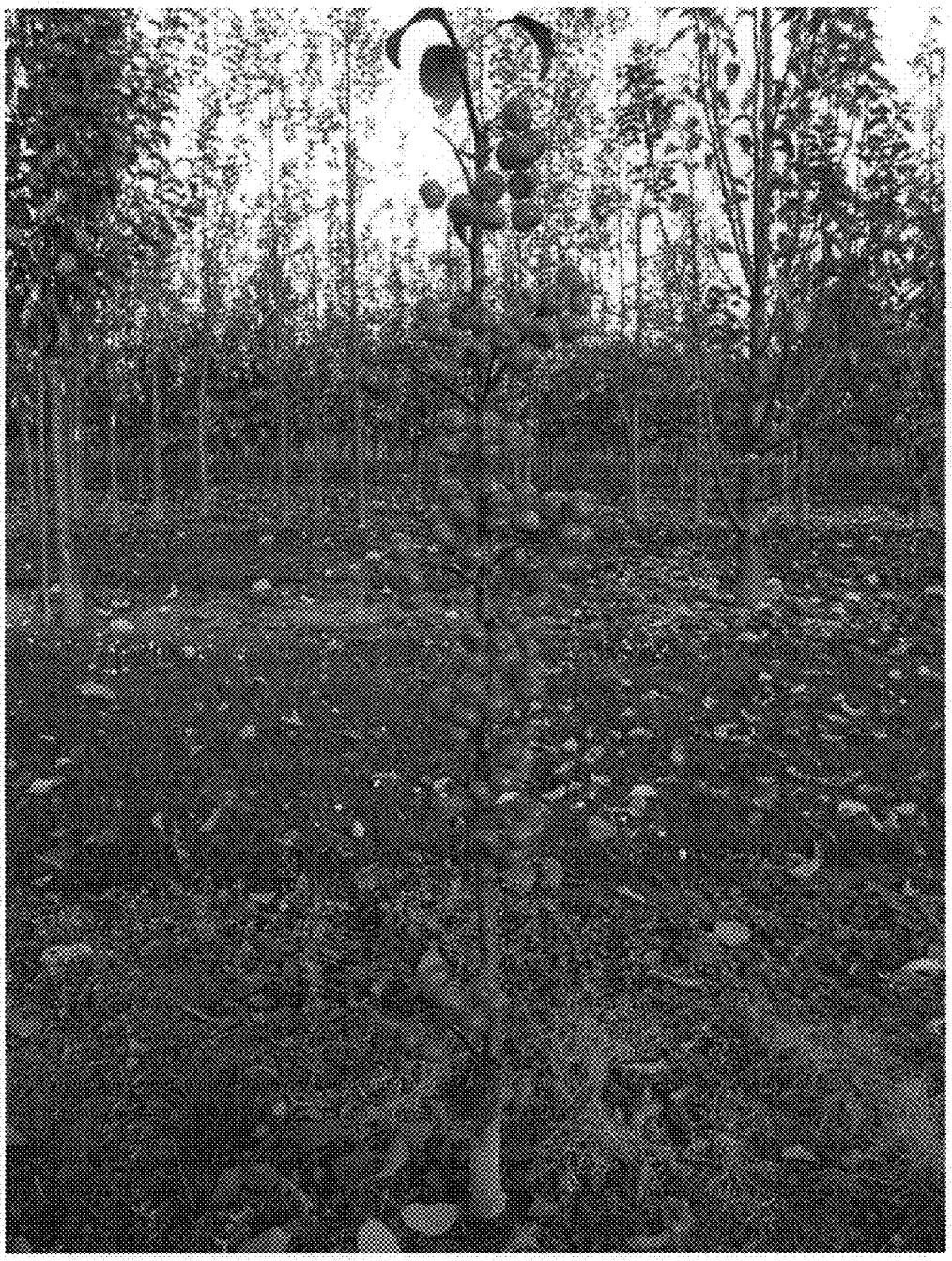
FIG. 3 illustrates a young tree of the new variety at 4 years of age, demonstrating that the fruits are persistent on the tree after its leaves fall until the end of Winter.
Figure 4:
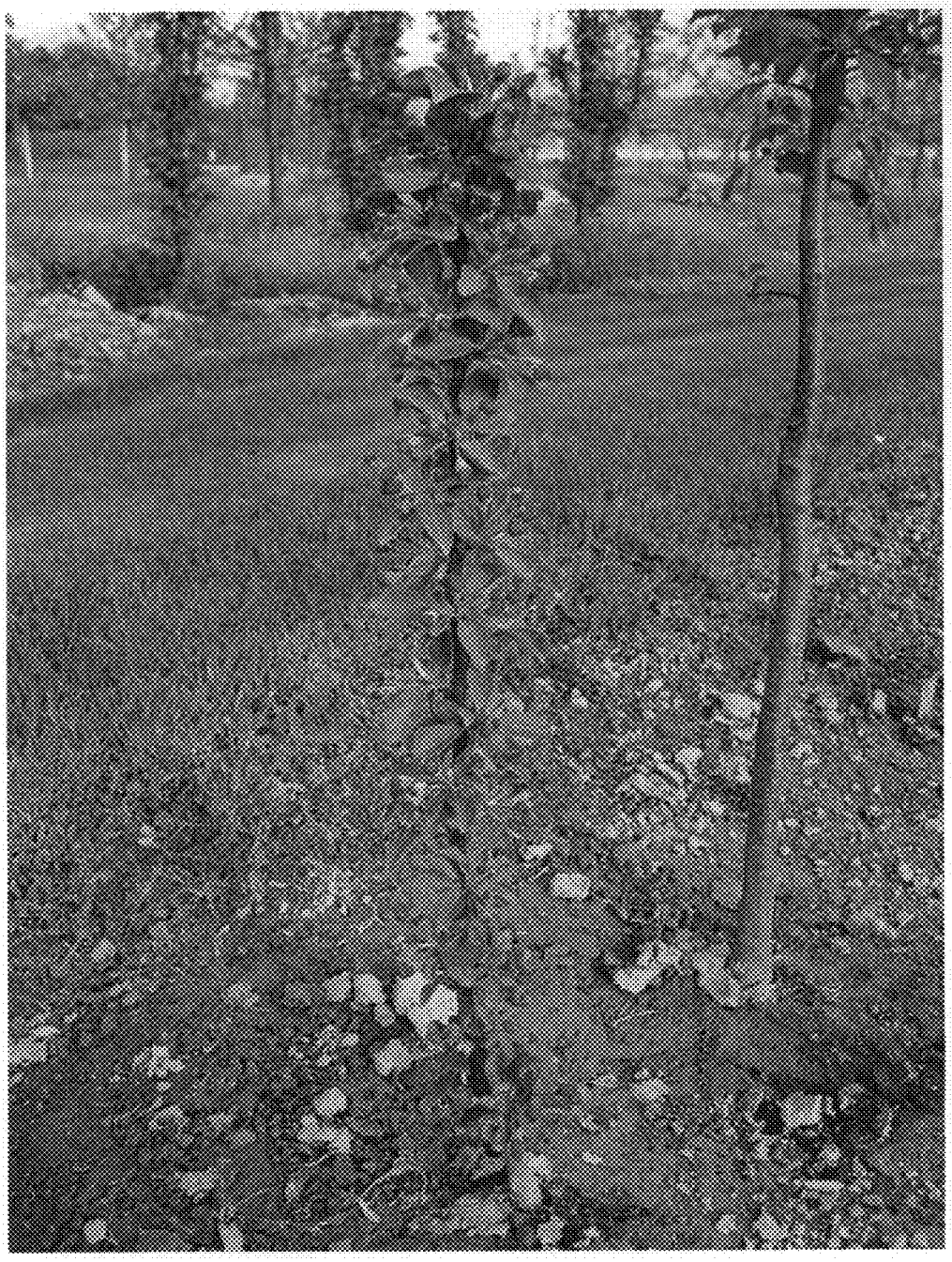
FIG. 4 illustrates a young tree of the new variety grafted on MM 106 rootstock at 2 years from grafting, at first flower opening.
Figure 5:
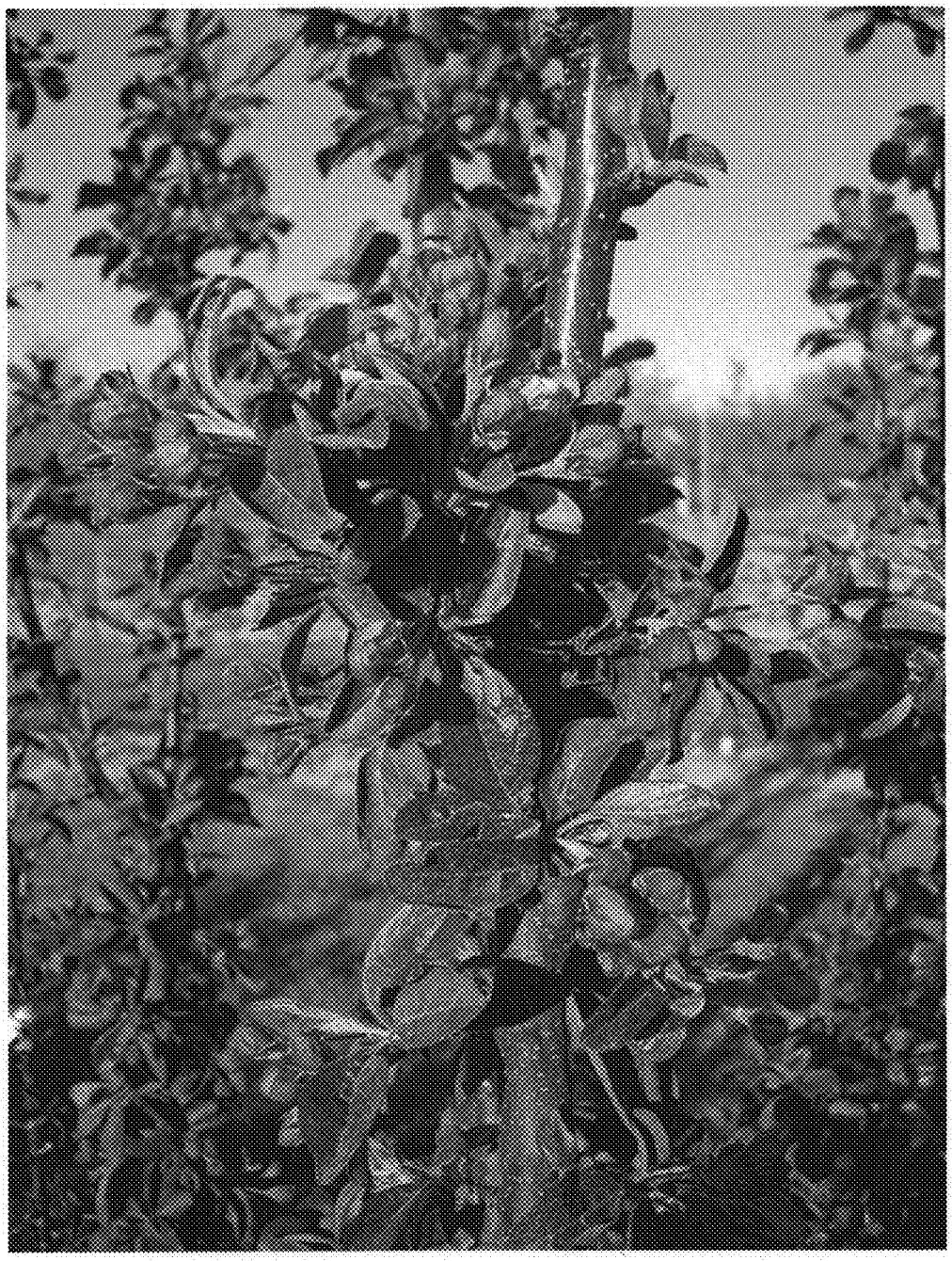
FIG. 5 illustrates a section of the vertical trunk of the new variety at 3 years of age, showing predominantly unopened flowers at the beginning of blossoming time.
Figure 6:
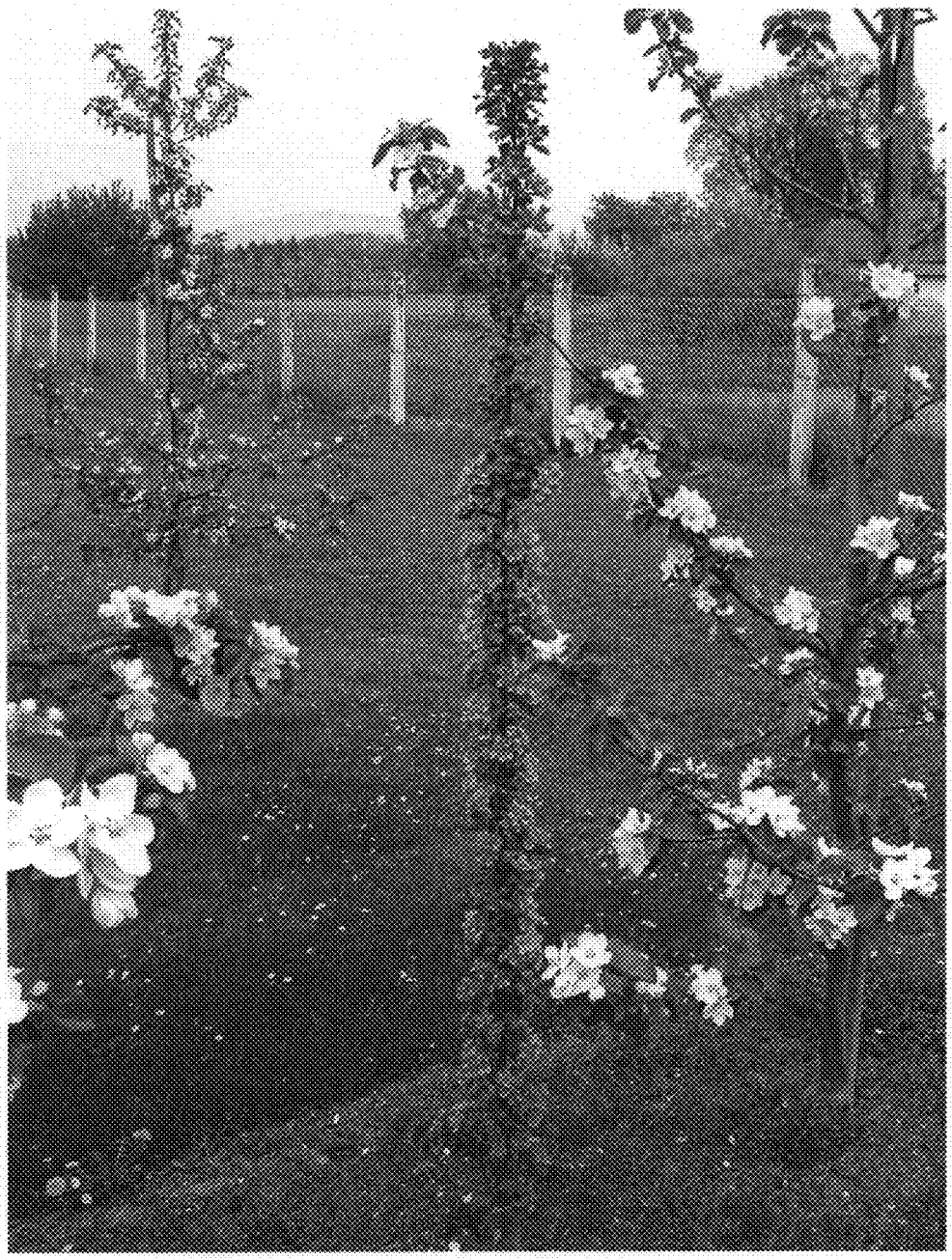
FIG. 6 illustrates a tree of the new variety grafted on MM 106 rootstock at 5 years of age, showing its canopy form with fully opened flowers.
Figure 7:
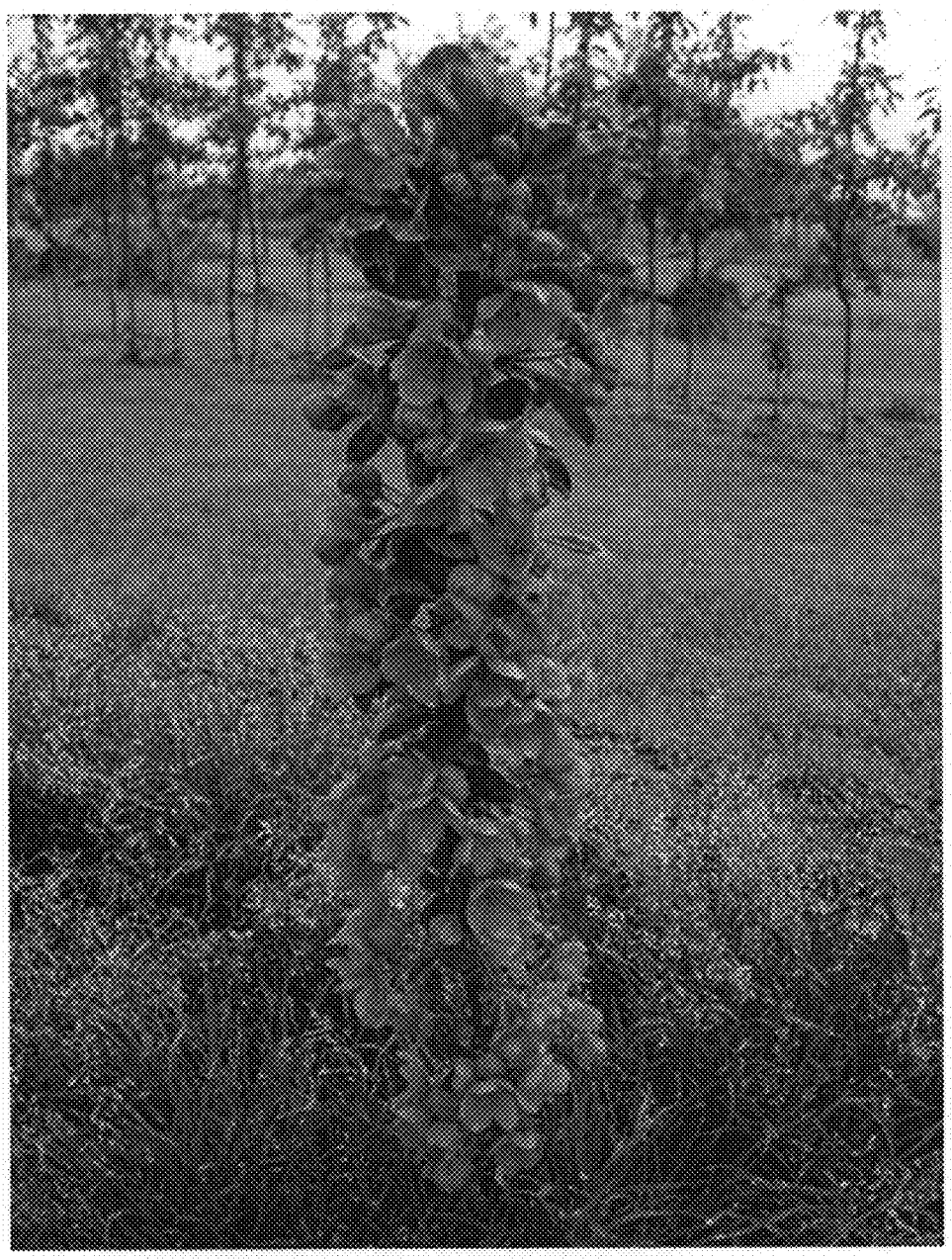
FIG. 7 illustrates a young, flowering tree grafted on MM 106 rootstock at 5 years of age.
Figure 8:
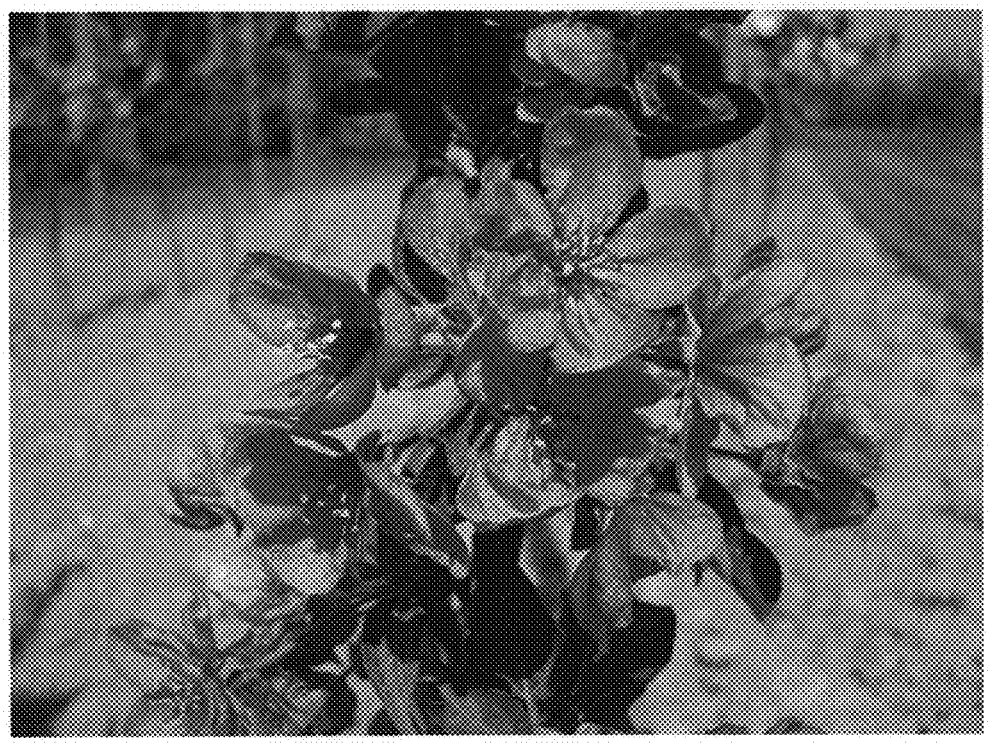
FIG. 8 illustrates details of fully opened flowers of the new variety from a 3-year old tree.

The following detailed description sets forth characteristics of the new cultivar. The new variety was grown under natural field conditions in The Czech Republic. The following fertilizer combination was used (Kg/ha/year): 55 parts nitrogen, 25 parts phosphorous, 60 parts potassium, 55 parts calcium, and 5 parts magnesium. Color references are primarily to The 1986 R.H.S. Colour Chart of The Royal Horticultural Society of London (in association with the Flower Council of Holland), Second Edition, and were identified under natural light.

Tree:

*Age*.—Approximately 4 years.

*Size*.—Crown height of 2.0 m, width of 0.25 m.

*Vigor*.—Weak to medium.

*Density*.—Compact and only vertical.

*Form*.—Erect, compact, and free of side branches.

*Production*.—Very precocious.

*Growth type*.—Columnar.

*Bearing*.—Annual; predominantly on spurs.

*Average productivity*.—4 kg per 5-year old tree.

Trunk:

*Size*.—Approximately 4.5 cm in diameter at 30.0 cm from the soil line.

*Surface texture*.—Smooth.

*Bark color*.—Greyed-Orange Group RHS 166A.

*Lenticels* (50.0 *cm above ground*).—Length: 1.0 mm to 2.0 mm. Width: 0.5 mm to 1.0 mm. Color: Greyed-Orange Group RHS 164B. Density: Variable, with 5 to 8 lenticels on average per 1 $cm^2$.

Branches: Not applicable—absent. The variety lacks a conventional branching system along the tree trunk.

Leaves:

*Length*.—80.0 mm to 100.0 mm, averaging about 95.0 mm.

*Width*.—44.0 mm to 57.0 mm, averaging about 50.0 mm.

*Form*.—Ellipsoidal, elongated, seldom ovate.

*Texture*.—Smooth.

*Thickness*.—Thin to medium.

*Base*.—Cuneate, often asymmetric.

*Apex*.—Acuminate.

*Margin*.—Serrate.

*Attitude of leaf blade in relation to the shoot*.—Young leaves: Outwards. Mature leaves: Outwards to downwards.

*Pubescence*.—Upper surface: None. Lower surface: Very fine.

*Color*.—Young leaves: Upper surface: Greyed-Purple Group RHS 187A. Lower surface: Greyed-Purple Group RHS 187A to 187B. Mature leaves: Upper surface: Yellow-Green Group RHS 147A. Lower surface: Yellow-Green Group RHS 148A.

*Petiole*.—Shape: Straight with thickening and flattening of the base. Length: 35.0 mm to 62.0 mm, averaging about 48.0 mm. Diameter: 1.2 mm to 1.8 mm, averaging about 1.5 mm. Color: Red-Purple Group RHS 59B generally, with Red-Purple Group RHS 59A present at the base.

*Stipule*.—Length: 0.7 cm. Shape: Ellipsoid, with an acute apex. Color: Yellow-Green Group RHS 147A.

*Veins*.—Description: Well proportioned, medium dense, with pinnate main veins and netted minor veins. Color: Upper surface: Red-Purple Group RHS 59B. Lower surface: Red-Purple Group RHS 59C.

Flower buds:

*Pedicel*.—Length: Typically in the range of 13.0 mm to 22.0 mm, with an average of 15.0 mm. Diameter: 1.0 mm on average. Color: Predominantly Red-Purple Group RHS 59A.

*Bud*.—Length: 1.0 mm on average. Width: 10.0 mm on average. Color: Predominantly Red-Purple Group RHS 59B to 59C.

Flowers:

*Bloom timing*.—At the end of April/4$^{th}$ of May — about the same time or two days before 'Golden Delicious'.

*Blooming period*.—Medium to long.

*Pollination requirements*.—Self-sterile, needs pollinators such as *Malus* x *zumi* (crab apple) 'Professor Sprenger' (unpatented).

*Number of flowers per cluster*.—5 to 7.

*Fragrance*.—Faint.

*Average diameter*.—4.1 cm.

*Petals*.—Number: 5. Length: From 20.0 mm to 26 0 mm, with an average of 22.0 mm. Width: From 13.0 mm to 16 0 mm, with an average of 15.0 mm. Shape: Oval. Apex: Obtuse. Base: Mucronate. Aspect: Positioned overlapping to touching. Margin: Entire. Texture and appearance: Soft, slightly rumpled, and smooth. Color: When opening: Upper surface: Red-Purple Group RHS 64B. Lower surface: Red-Purple Group RHS 64B. Fully opened: Upper surface: Red-Purple Group RHS 60C to 60D. Lower surface: Red-Purple Group RHS 60C to 60D.

*Sepals*.—Number: 5 (average). Shape: Long-conical; pointed. Margin: Entire. Texture: Finely pubescent. Length: 7.0 mm to 9.0 mm, average of 8.0 mm from the union. Width: 3.0 mm in the middle. Color: Upper surface: Green Group RHS 138B, with a Red-Purple Group RHS 59A apex. Lower surface: Red-Purple Group RHS 59A.

*Stamens*.—Number (per flower): Average of 19. Filament length: 7.0 mm to 11.0 mm.

*Anthers*.—Shape: Oval. Length: 2.0 mm. Color: Yellow Group RHS 10C.

*Pollen*.—Color: Yellow Group RHS 10B. Amount (generally): Medium to high.
*Pistils*.—Length: 11.0 mm on average.
*Style*.—Length: 9.0 mm on average. Color: Red Group RHS 51C.
*Stigma*.—Shape: Rounded at the top. Color: Yellow-Green Group RHS 151B.

Fruit:
*Bearing*.—Predominantly on spurs.
*Maturity when described*.—Harvest maturity (date of picking).
*Date of picking*.—Oct. 30, 2018.
*Size*.—Axial diameter: 17.0 mm to 22.5 mm, averaging about 20.0 mm. Transverse diameter: 23.0 mm to 27.0 mm, averaging about 25.0 mm.
*Weight per fruit*.—Average of 6 g.
*Form*.—Globose to obloid.
*Cavity*.—Shape: Funnel, shallow, russet free. Depth: 1.8 mm on average. Breadth: 6.0 mm on average.
*Basin*.—Shape: Slightly raised above the surface of the fruit, with slight humps. Depth: Not measurable. Width: Not measurable.
*Calyx*.—Persistent with erect lobes.

Skin:
*Thickness*.—Medium.
*Texture*.—Smooth, free of russet.
*Tendency to crack*.—Absent.
*Overcolor*.—Red-Purple Group RHS 59A, covers almost the entire fruit (95-100%).
*Ground color*.—Red Group RHS 45C on average, rarely present on a small area of the fruit.
*Young fruit anthocyanin overcolor*.—100% presence with very dark and high intensity.
*Lenticels*.—Average number per fruit: 354. Average length: 0.42 mm. Average width: 0.40 mm. Color: Orange-White Group RHS 159A to 159B.

Flesh:
*Aroma*.—Weak, like an ornamental apple.
*Color*.—Red Group RHS 53A to 53B.
*Texture*.—Medium grained, firm.
*Eating quality*.—Not applicable, an ornamental variety.

Core:
*Bundle area*.—Onion-shaped on longitudinal section.
*Aperature of the locules in the transverse section*.—Mostly moderately open, rarely slightly open.
*Bundle*.—Vascular strands are weakly to moderately defined.
*Calyx tube*.—Short.
*Depth of tube to shoulder*.—3.5 mm on average.
*Styles*.—Persistent as dry residues, closed with calyx lobes.
*Stamens*.—Persistent as dry residues, closed with calyx lobes.
*Seed cells*.—Wall: Smooth. Depth: 3.0 mm on average. Breadth: 4.0 mm on average. Longitudinal section: 6.0 mm to 9.0 mm, averaging about 7.0 mm.

Seeds:
*Number perfect*.—7 to 10.
*Number in one cell*.—1 to 2.
*Length*.—5.0 mm on average.
*Breadth*.—3.0 mm on average.
*Form*.—Ovoid with an obtusely pointed tip.
*Color*.—Greyed-Orange Group RHS 175A to 172A.

Stem:
*Length*.—17.0 mm to 32.0 mm, averaging about 25.0 mm.
*Width*.—0.8 mm to 1.2 mm, averaging about 1.0 mm.
*Color*.—Red Group RHS 53A to Greyed-Purple Group RHS 187A.

General:
*Use*.—As an ornamental variety having a columnar tree growth type.
*Shipping quality*.—Not applicable — ornamental variety.
*Keeping quality*.—Not applicable — ornamental variety.
*Tree winter hardiness*.—No frost damage observed at the place of origin, lowest winter temperatures approximately −20° C.
*Bud winter hardiness*.—No frost damage observed at the place of origin, lowest winter temperatures approximately −20° C.
*Drought tolerance*.—Unknown.
*Disease resistance*.—$V_f$-resistance against scab.

We claim:

1. A new and distinct variety of *Malus domestica* (Borkh.) apple tree plant substantially as is herein described and illustrated.

* * * * *